United States Patent
Roxhead et al.

(10) Patent No.: US 11,254,488 B2
(45) Date of Patent: Feb. 22, 2022

(54) SPRAY NOZZLE CHIP AND A MEDICAMENT DELIVERY DEVICE COMPRISING THE SAME

(71) Applicant: SHL MEDICAL AG, Zug (CH)

(72) Inventors: Niclas Roxhead, Bromma (SE); Torben Last, Osterode am Harz (DE); Göran Stemme, Lidingö (SE)

(73) Assignee: SHL MEDICAL AG, Zug (CH)

( * ) Notice: Subject to any disclaimer, the term of this patent is extended or adjusted under 35 U.S.C. 154(b) by 29 days.

(21) Appl. No.: 16/954,712

(22) PCT Filed: Dec. 5, 2018

(86) PCT No.: PCT/EP2018/083702
§ 371 (c)(1),
(2) Date: Jun. 17, 2020

(87) PCT Pub. No.: WO2019/121025
PCT Pub. Date: Jun. 27, 2019

(65) Prior Publication Data
US 2020/0385201 A1 Dec. 10, 2020

(30) Foreign Application Priority Data
Dec. 21, 2017 (EP) .................................... 17209321

(51) Int. Cl.
*B05B 1/34* (2006.01)
*B65D 83/14* (2006.01)
(Continued)

(52) U.S. Cl.
CPC ....... *B65D 83/7535* (2013.01); *A61M 11/006* (2014.02); *B05B 1/14* (2013.01); *B05B 1/323* (2013.01); *B05B 15/40* (2018.02)

(58) Field of Classification Search
CPC ......... B05B 1/14; B05B 1/323; B05B 1/3436; B05B 15/40; B05B 11/0064;
(Continued)

(56) References Cited

U.S. PATENT DOCUMENTS 2,273,830 A * 2/1942 Brierly ................... B21D 53/00
29/890.02
2,308,476 A * 1/1943 Gerrer ...................... B05B 1/00
239/533.14
(Continued)

FOREIGN PATENT DOCUMENTS

DE 19911805 A1 9/2000
GB 2539512 A 12/2016
(Continued)

OTHER PUBLICATIONS

International Search Report and Written Opinion for Int. App. No. PCT/EP2018/083702, completed Feb. 12, 2019.

*Primary Examiner* — Charles P. Cheyney
(74) *Attorney, Agent, or Firm* — McDonnell Boehnen Hulbert & Berghoff LLP

(57) ABSTRACT

A spray nozzle chip is presented having: a first layer provided with a first layer orifice, a mechanically flexible nozzle layer provided with a nozzle orifice, the spray nozzle chip having a valve functionality obtained by movement of the nozzle layer relative to the first layer due to pressure changes, wherein the nozzle orifice is closed when the nozzle layer is in a default non-pressurised state and wherein the nozzle orifice is opened and set in fluid communication with the first layer orifice when the nozzle layer is deformed due to pressure during a spraying operation, and wherein the spray nozzle chip further has a sealing layer configured to rupture when the nozzle layer is deformed due to applied pressure during a spraying operation.

20 Claims, 4 Drawing Sheets

(51) Int. Cl.
*A61M 11/00* (2006.01)
*B05B 15/40* (2018.01)
*B05B 1/14* (2006.01)
*B05B 1/32* (2006.01)

(58) Field of Classification Search
CPC . A61M 11/006; B65D 83/7535; B65D 83/20; F02M 61/1853; F02M 61/047; F02M 61/166
USPC .............................. 222/494, 380, 496, 402.1
See application file for complete search history.

(56) References Cited

U.S. PATENT DOCUMENTS

| | | | | |
|---|---|---|---|---|
| 2,805,891 A * | 9/1957 | Sanborn | ............... | F02M 61/047 239/533.9 |
| 4,313,568 A * | 2/1982 | Shay | ........................ | B05B 1/12 222/380 |
| 4,358,057 A * | 11/1982 | Burke | ...................... | B05B 1/12 222/380 |
| 4,756,508 A * | 7/1988 | Giachino | .............. | B41J 2/17596 239/102.2 |
| 4,768,717 A * | 9/1988 | Shay | ..................... | B05B 7/0056 239/403 |
| 5,370,318 A * | 12/1994 | Weston | ............... | B05B 11/3077 239/533.14 |
| 5,435,884 A * | 7/1995 | Simmons | ........... | F02M 61/1853 216/100 |
| 5,752,626 A * | 5/1998 | Bachand | ............... | B05B 1/3436 222/136 |
| 6,464,150 B1 | 10/2002 | Zimmer et al. | | |
| 2003/0178507 A1 | 9/2003 | Van | | |
| 2016/0175863 A1* | 6/2016 | Bloc | ................... | B05B 11/0005 222/190 |

FOREIGN PATENT DOCUMENTS

| | | |
|---|---|---|
| WO | 94/22412 A1 | 10/1994 |
| WO | 2007/007575 A1 | 1/2007 |
| WO | 2016/203225 A1 | 12/2016 |
| WO | 2017/095220 | 6/2017 |

* cited by examiner

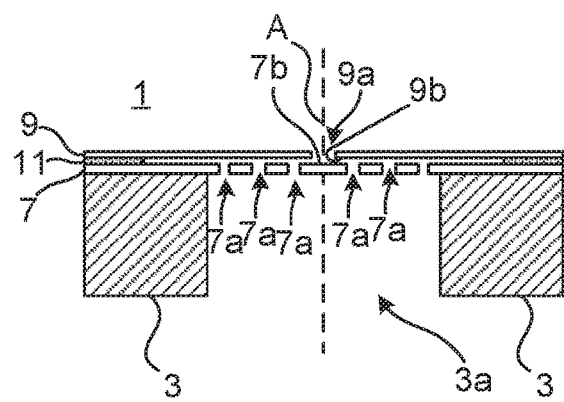
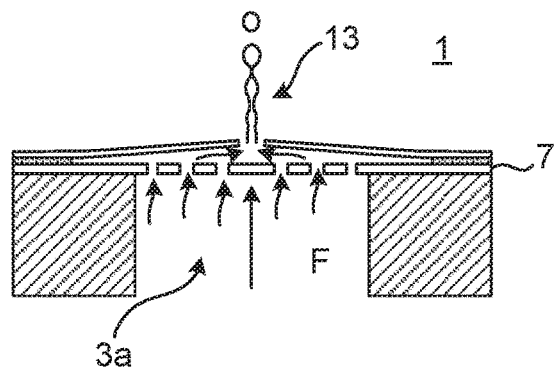
Fig. 1a  Fig. 1b
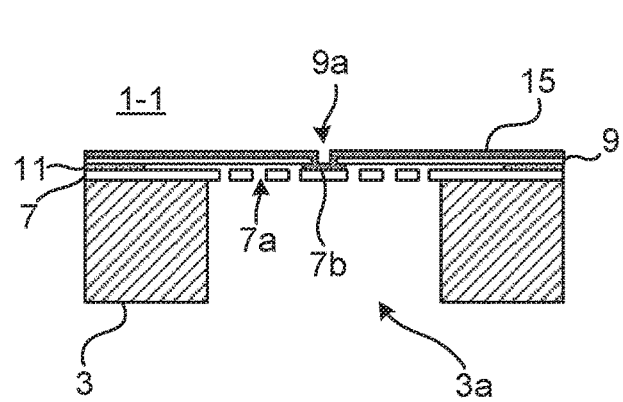
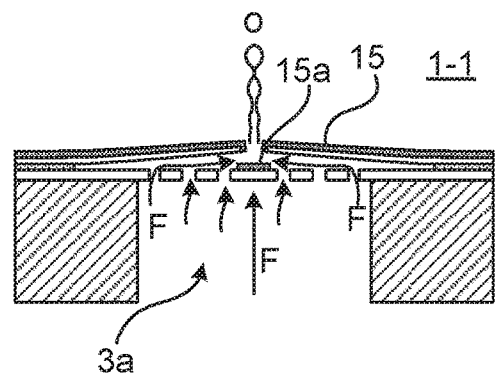
Fig. 2a  Fig. 2b
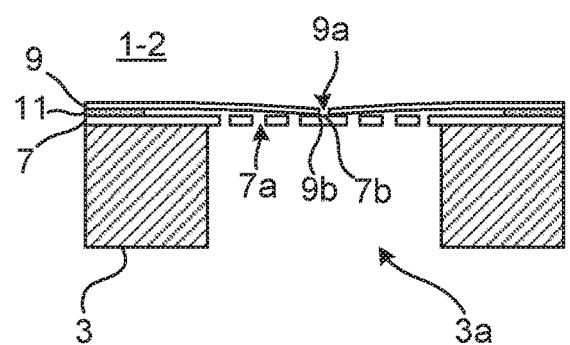
Fig. 3

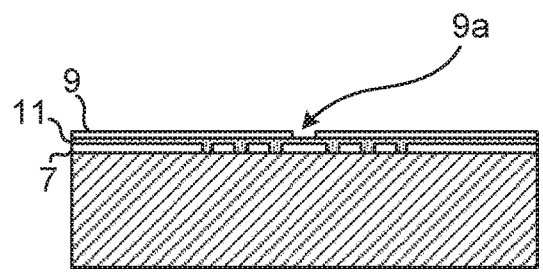
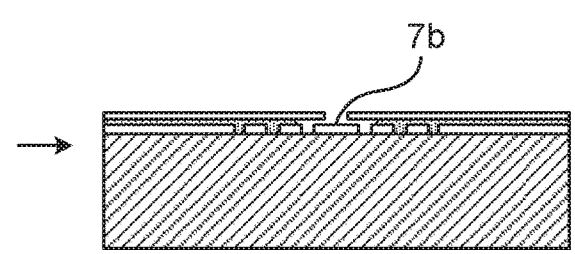
Fig. 7a	Fig. 7b
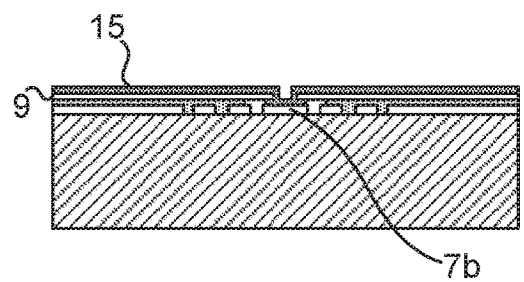
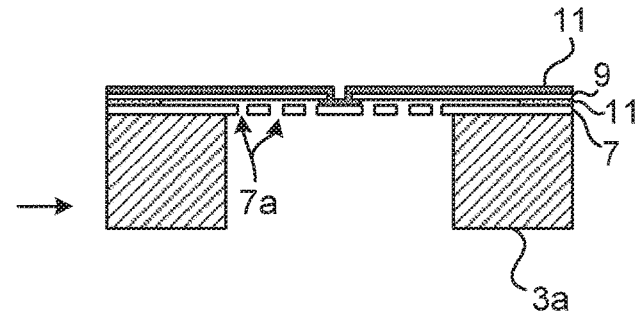
Fig. 7c	Fig. 7d
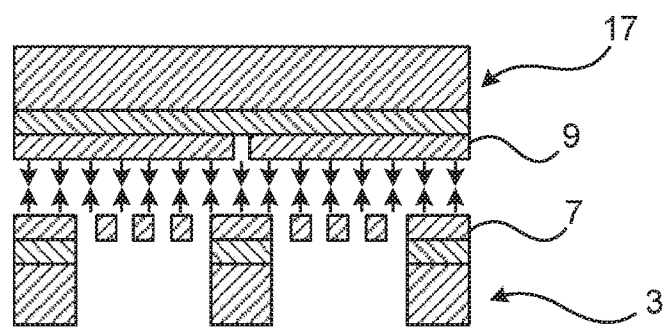
Fig. 8

SPRAY NOZZLE CHIP AND A MEDICAMENT DELIVERY DEVICE COMPRISING THE SAME

CROSS REFERENCE TO RELATED APPLICATIONS

The present application is a U.S. National Phase Application pursuant to 35 U.S.C. § 371 of International Application No. PCT/EP2018/083702 filed Dec. 5, 2018, which claims priority to European Patent Application No. 17209321.3 filed Dec. 21, 2017. The entire disclosure contents of these applications are herewith incorporated by reference into the present application.

TECHNICAL FIELD

The present disclosure generally relates to a spray nozzle chip, in particular for a medicament delivery device.

BACKGROUND

A nozzle device may be configured to atomise a fluid, i.e. to make an aerosol of the fluid. A nozzle device of this type may comprise a sieve membrane provided for filtering out any undesired larger particles contained in the fluid to be atomised. The nozzle device may also include a nozzle membrane with one or more orifices. The nozzle membrane and the sieve membrane are configured to be in fluid communication. In the process of atomisation, the fluid first passes the sieve membrane. The filtered fluid subsequently passes through the one or more orifices of the nozzle membrane, whereby the fluid is atomised.

An example of a spray device is disclosed in WO 2017/095220 A1. The spray device comprises a spray nozzle body and a substantially planar membrane suspended over a nozzle cavity to generate microjets, in particular for pharmaceutical applications. The nozzle body contains a microbial barrier in form of a microvalve between a fluid supply channel and the nozzle cavity.

The nozzle cavity provides a risk with respect to microbial safety of the spray device, because the cavity is in contact with the outside environment. Additionally, the configuration disclosed in WO 2017/095220 A1 provides a single fluid flow to a plurality of nozzle orifices distributed circularly around the microvalve. The force required to open the valve is provided only in the valve seat, which covers only part of the membrane, thus requiring a relatively high fluid pressure during spraying to operate as intended.

WO 2016/203225 shows a nozzle assembly having a valve and filter functionality adapted for larger dimensions and higher pressures, which allows the use of other materials and processes than available for the present disclosure.

SUMMARY

In view of the above, a general object of the present disclosure is to provide a spray nozzle chip which solves or at least mitigates problems of the prior art.

There is hence according to a first aspect of the present disclosure provided a spray nozzle chip, comprising: a first layer provided with a first layer orifice, a mechanically flexible nozzle layer provided with a nozzle orifice, the spray nozzle chip having a valve functionality obtained by movement of the nozzle layer relative to the first layer due to pressure changes, wherein the nozzle orifice is closed when the nozzle layer is in a default non-pressurised state and wherein the nozzle orifice is opened and set in fluid communication with the first layer orifice when the nozzle layer is deformed due to pressure during a spraying operation.

The relative movement between the first layer and the nozzle layer provides a closure of the nozzle orifice when the nozzle layer is in the default non-pressurised state. Since the nozzle orifice is closed in this state, the exposure to the outside environment is minimised with only the nozzle orifice being exposed. In WO 2017/095220 A1, the nozzle cavity below the nozzle orifice is also exposed to the outside world. The nozzle cavity will thereby be contaminated by drying fluid. If reused, the fluid has to pass the contaminated nozzle cavity. Hereto, the present spray nozzle chip may provide a better microbial protection.

The nozzle orifice and the first layer orifices diameters may for example be of the order of micrometres. More specifically, the nozzle orifice and/or the first layer orifices may have a diameter of 0.1-50 µm, or 0.1-25 µm, or 0.1-10 µm, or 0.1-5 µm, or 0.5-3 µm, or 0.5-1.5 µm. The length or depth of the nozzle orifice and/or the first layer orifices may for example be between 0.2-20 µm, or 0.2-10 µm, or 0.2-5 µm or 0.5-3 µm, or 0.5-2 µm.

The fluid may be a liquid, for example a liquid medicament.

According to one embodiment the nozzle orifice has a nozzle orifice perimeter and wherein the nozzle orifice and the nozzle orifice perimeter are covered in the default non-pressurised state due to cooperation between the nozzle layer and the first layer.

The nozzle orifice may be arranged symmetrically with respect to a fluid supply orifice causing the ventilation functionality in the region where the nozzle layer is deformed the most. This is where the lifting action is the greatest. The lifting force thus acts on a majority of the nozzle layer, in contrast to WO 2017/095220 A1, where the lifting action is limited to the central region of the membrane layer, where the microvalve is located. The same amount of nozzle layer displacement during a spraying operation opens the nozzle orifice more than is the case in WO 2017/095220. Lower pressure is hence necessary to obtain the necessary opening for fluid spraying.

According to one embodiment the nozzle orifice perimeter is in contact with the first layer in the default non-pressurised state to thereby close the nozzle orifice. The entire nozzle orifice perimeter may be in contact with the first layer during the default non-pressurised state. The contact with the first layer may be direct or indirect.

If the nozzle layer comprises a plurality of nozzle orifices, preferably each nozzle orifice is individually closed when the nozzle layer is in the default non-pressurised state and each nozzle orifice is opened and set in communication with the first layer orifice when the nozzle layer is deformed due to pressure during a spraying operation.

One embodiment comprises a sealing layer configured to seal the nozzle orifice before initial use of the spray nozzle chip, the sealing layer being configured to rupture when the nozzle layer is deformed due to applied pressure during a spraying operation. The sealing layer could be hermetic or non-hermetic, e.g. providing only a moisture, fluid or particle seal, or combinations thereof. By hermetically sealing the nozzle orifice before initial use, a medicament delivery device comprising the spray nozzle chip may be stored for a longer period of time than is possible today. Furthermore, it could enable the reuse of the spray nozzle chip for medical drug delivery.

According to one embodiment the sealing layer is antibacterial. The storage time may thereby be even further increased.

According to one embodiment the sealing layer comprises silver and/or a hydrophobic component. By using a hydrophobic component in the sealing layer, fluid droplets will be repelled from the sealing layer also after the hermetic sealing layer has ruptured. The risk of microbial growth may thereby be reduced. Additionally, the risk that the nozzle orifice becomes occluded is also reduced.

According to one embodiment the nozzle layer is mechanically more flexible than the first layer.

According to one embodiment each of the first layer and the nozzle layer is a membrane layer.

According to one embodiment the first layer is generally parallel with the nozzle layer.

The first layer may have a first layer inner surface and the nozzle layer may have a nozzle layer inner surface facing the first layer inner surface. The first layer inner surface and the nozzle layer inner surface may be configured to be in contact along essentially their entire respective surface areas when the nozzle layer is in the default non-pressurised state. In this case, portion of or the entire surface of one or both of the nozzle layer inner surface and the first layer inner surface may be geometrically or chemically modified so that they do not stick or attach to each other when in direct contact.

According to one embodiment the spray nozzle chip may comprise a support layer provided between a portion of the first layer and the nozzle layer to distance the nozzle layer from the first layer. The support layer may be in the order of Angstrom. The support layer may be a thin film layer.

According to one embodiment the nozzle orifice has a nozzle orifice perimeter, and the nozzle layer has an internal built-in stress that presses the nozzle layer to the first layer in the default non-pressurised state to thereby cover the nozzle orifice and the nozzle orifice perimeter. The nozzle layer may hence close the nozzle orifice as it is pressed against the first layer due to the internal stress in the default non-pressurised state, i.e. when the fluid is not pressurised. This may provide enhanced closing of the nozzle orifice when not in use. The built-in stress in the nozzle layer may for example be obtained by a bimorph structure or induced residual stress during manufacturing.

According to one embodiment one of the first layer and the nozzle layer has a protruding structure that encircles the perimeter of the nozzle orifice and provides a sealing pressure to close the nozzle orifice in the default non-pressurised state.

One embodiment comprises a substrate supporting the first layer, which substrate is provided with a fluid supply orifice configured to supply fluid to the first layer orifice.

The nozzle orifice may be centred with respect to the fluid supply orifice. The nozzle layer will thereby be deformed, or lifted, relative to the first layer maximally in the region of the nozzle orifice. Alternatively, the substrate may be provided with a plurality of fluid supply orifices and the nozzle orifice may be aligned with a separating wall between the fluid supply orifices, in the axial direction of the spray nozzle chip.

According to one embodiment the cross-sectional area of the first layer orifice is smaller than the cross-sectional area of the nozzle orifice.

According to one embodiment the first layer is a sieve layer comprising a plurality of first layer orifices configured to be in communication with the nozzle orifice when the nozzle layer is deformed due to pressure during a spraying operation.

The number of first layer orifices may be larger than the number of nozzle orifice(s). A lower pressure drop over the first layer may thereby be obtained.

The first layer orifice area formed by all the first layer orifices is preferably larger than the nozzle orifice area formed by all the nozzle orifice(s).

There is according to a second aspect of the present disclosure provided a medicament delivery device comprising a spray nozzle chip according to the first aspect.

According to one embodiment the medicament delivery device is an inhaler or an eye dispenser.

There is according to a third aspect of the present disclosure provided a method of manufacturing a spray nozzle chip according to the first aspect, wherein the method comprises: performing a first deposition onto a substrate to obtain a first layer, providing the first layer with a first layer orifice, performing a third deposition onto the first layer to obtain a nozzle layer, providing the nozzle layer with a nozzle orifice, and providing a fluid supply orifice in the substrate, the fluid supply orifice being set in fluid connection with the first layer orifice.

The first layer and the nozzle layer may for example be bonded together using fusion bonding, adhesive bonding, eutectic bonding, surface activated bonding, plasma activated bonding, etc. The bonding can be made selectively to enable the valve functionality of the spray nozzle chip. Hereto, the bonding is typically made in lateral regions of the first layer and the nozzle layer, usually in regions aligned with the substrate and distanced from the region which comprises the nozzle orifice and the first layer orifice(s).

One embodiment comprises performing a fourth deposition onto the nozzle layer to obtain a sealing layer, before providing a fluid supply orifice in the substrate.

According to one embodiment the fluid supply orifice may be provided in the substrate by means of etching.

One embodiment comprises performing a second deposition onto the first layer to obtain a support layer, after the first layer has been provided with a first layer orifice and before the third deposition. The support layer may for example form an intermediate, adhesive or eutectic bonding layer.

One embodiment may comprise creating a separation or distancing of the first layer and the nozzle layer by removing a portion of the support layer. The support layer may thus be undercut. The undercutting may for example be obtained using wet or dry etching.

Another method of manufacturing a spray nozzle chip according to the first aspect comprises: providing a first substrate with a first layer with first layer orifices, providing a second substrate with a nozzle layer with nozzle layer orifices, and transferring the nozzle layer onto the first layer to obtain the spray nozzle chip.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which:

FIG. 1a schematically shows a section of a spray nozzle chip in a default non-pressurised state;

FIG. 1b schematically shows the spray nozzle chip in FIG. 1a during a spraying operation;

FIG. 2a schematically shows a longitudinal section of another example of a spray nozzle chip in a default non-pressurised state;

FIG. 2b schematically shows the spray nozzle chip in FIG. 2a during a spraying operation;

FIG. 3 schematically depicts a section of yet another example of a spray nozzle chip;

FIG. 7a schematically shows section of the spray nozzle chip in FIGS. 2a and 2b during manufacturing thereof;

FIG. 7b schematically shows a section of the spray nozzle chip in FIGS. 2a and 2b during manufacturing thereof;

FIG. 7c schematically shows a section of the spray nozzle chip in FIGS. 2a and 2b during manufacturing thereof;

FIG. 7d schematically shows a section of the spray nozzle chip in FIGS. 2a and 2b during manufacturing thereof;

FIG. 8 shows an example of a particular manufacturing step of a spray nozzle chip.

DETAILED DESCRIPTION

Figure 4A:
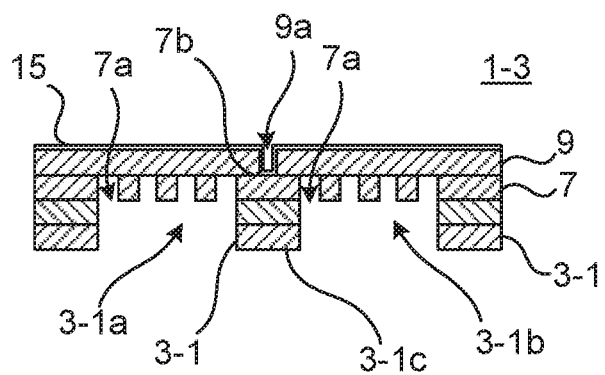
FIG. 4a schematically shows longitudinal sections of another example of a spray nozzle chip in a default non-pressurised state and during a spraying operation, respectively.
Figure 5A:
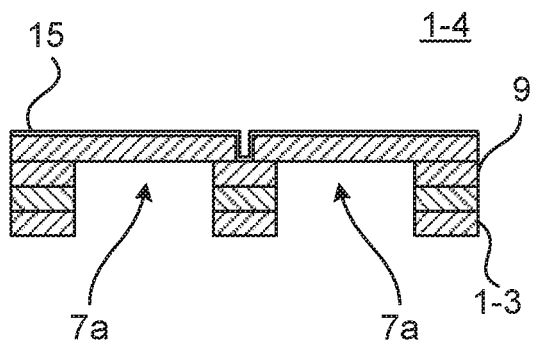
FIG. 5a schematically shows longitudinal sections of yet another example of a spray nozzle chip in a default non-pressurised state and during a spraying operation, respectively.
Figure 4B:
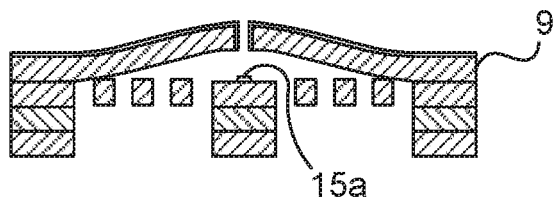
FIG. 4b schematically shows longitudinal sections of another example of a spray nozzle chip in a default non-pressurised state and during a spraying operation, respectively.
Figure 5B:
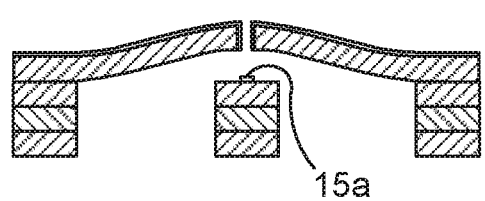
FIG. 5b schematically shows longitudinal sections of yet another example of a spray nozzle chip in a default non-pressurised state and during a spraying operation, respectively.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

FIG. 1a shows an example of a spray nozzle chip. The spray nozzle chip 1 is configured to be installed in a medicament delivery device.

The exemplified spray nozzle chip 1 comprises a substrate 3 having a fluid supply orifice 3a, which extends through the substrate 3. The substrate 3 may for example be made of a ceramic material such as silicon. The spray nozzle chip 1 furthermore comprises a first layer 7 and a nozzle layer 9. The nozzle layer 9 is mechanically flexible. In particular, it is mechanically more flexible than the first layer 7. According to the example, the first layer 7 is a membrane layer. The nozzle layer 9 is a membrane layer.

In FIG. 1a, the spray nozzle chip 1 is shown when the pressure acting on the first layer 7 is essentially zero. The nozzle layer 9 is thus in a default non-pressurised state. This is generally the case when the spray nozzle chip 1 is not being used.

The first layer 7 is arranged on the substrate 3. The nozzle layer 9 is arranged on the first layer 7. In the present example, the spray nozzle chip 1 comprises a support layer, or intermediate layer, 11 configured to support the nozzle layer 9. The support layer 11 may be a thin film layer. The support layer 11 is arranged between a portion of the first layer 7 and the nozzle layer 9. The support layer 11 forms the attachment points of the nozzle layer 9, i.e. the nozzle layer 9 is attached to the support layer 11. Alternatively, the nozzle layer could be arranged directly on the first layer. In this case, it would be advantageous to modify the surface of at least one of the nozzle layer and the first layer so that they do not stick or attach to each other when the nozzle layer is to be deformed during a spraying operation.

The first layer 7 may be a sieve layer or filter layer. The first layer 7 comprises a plurality of first orifices 7a. The nozzle layer 9 comprises a nozzle orifice 9a. The nozzle orifice 9a has a nozzle orifice perimeter 9b. The nozzle orifice perimeter 9b discussed herein is the one which faces the underlying first layer 7.

Each first orifice 7a is smaller than or equal in size to the nozzle orifice 9a. In the former case, the cross-sectional area of any of the first orifices 7a is smaller than the cross-sectional area of the nozzle orifice 9a. The fluid supply orifice 3a has a larger cross-sectional area than the total cross-sectional area of the first orifices 7a. In the present example which comprises the support layer 11, the support layer 11 has a support layer orifice which has a larger cross-sectional area than the fluid supply orifice 3a. This does however not need to be the case.

The first orifices 7a and the nozzle orifice 9a are aligned with the fluid supply orifice 3a of the substrate 3. The fluid supply orifice 3a has a central axis A and the first orifices 7a and the nozzle orifice 9a all extend parallel with the central axis A. The first orifices 7a are arranged downstream of the fluid supply orifice 3a and the nozzle orifice 9a is arranged downstream of the first orifices 7a. The nozzle orifice 9a is in a direction parallel with the central axis A arranged aligned with a continuous surface of the first layer 7. Hereto, the nozzle orifice 9a is not aligned with any of the first orifices 7a. Although this is not shown in the schematic illustration in FIG. 1a due to the rather rough dimensioning of the support layer 11 in the drawing, the nozzle layer 9 bears against, i.e. is in direct contact with the first layer 7. In particular, the nozzle orifice perimeter 9b bears against the first layer 7. Since the first layer 7 defines a continuous surface 7b in the region which is aligned with the nozzle orifice 9a the nozzle orifice 9a and the nozzle orifice perimeter 9b are closed and covered by the first layer 7 in the default non-pressurised state of the nozzle layer 9 shown in FIG. 1a. This covering of the nozzle orifice 9 and the nozzle orifice perimeter 9a acts as a barrier against microbes when the spray nozzle chip 1 is not being used.

In the present example, the nozzle orifice 9a is intersected by a plane containing the central axis A. This plane may be centralised relative to the nozzle orifice 9a. The nozzle orifice 9a may be centralised relative to the fluid supply orifice 3a.

FIG. 1b shows the spray nozzle chip 1 during a spraying operation. The flow of a medicament fluid F is illustrated by a plurality of arrows. The fluid F flows through the fluid supply orifice 3*a* towards the first layer 7 and its plurality of first layer orifices 7*a*. The fluid F then flows through the first layer orifices 7*a*. This causes a pressure drop over the first layer 7. When the nozzle layer 9 is subjected to pressure in this situation, the nozzle layer 9 flexes away from the first layer 7. This leads to uncovering and thus opening of the nozzle orifice 9*a*, allowing the fluid F to flow through the nozzle orifice 9*a*. The nozzle layer 9 and the first layer 7 hence provide a valve functionality of the spray nozzle chip 1.

Figure 6A:
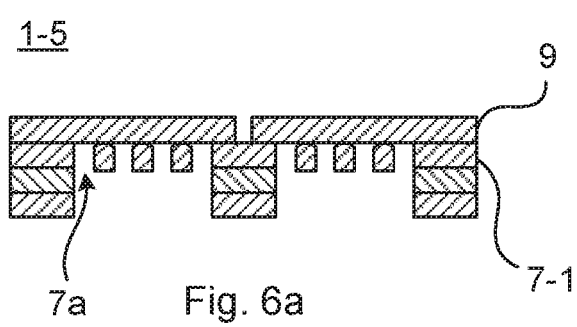
FIG. 6a schematically shows a further example of spray nozzle chips with geometric surface modifications.
Figure 6B:
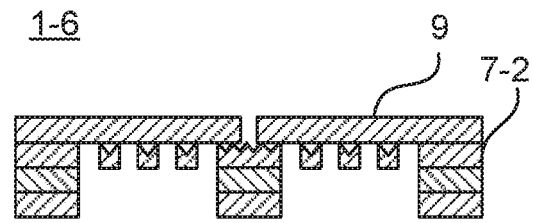
FIG. 6b schematically shows a further example of spray nozzle chips with geometric surface modifications.
Figure 6C:
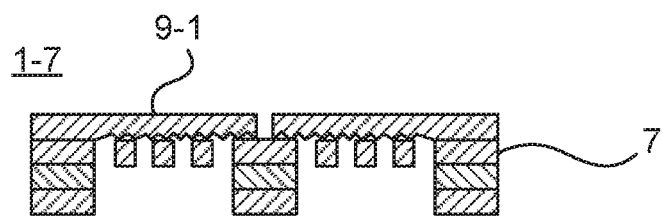
FIG. 6c schematically shows a further example of spray nozzle chips with geometric surface modifications.

After having passed the first layer orifices 7*a* the fluid F flows towards the nozzle orifice 9*a*. The fluid F exits the spray nozzle chip 1 through nozzle orifice 9*a*. Due to the aperture size of the nozzle orifice 9*a* and the pressure applied to the fluid, the exiting fluid jet breaks up into droplets 13, e.g. by Rayleigh breakup. Fluid F exiting through multiple nozzle orifices 9*a* forms an aerosol which may be inhaled, or applied as an eye spray, by a user. Once the spraying operation is completed and the pressure subsides, the nozzle layer 9 returns to its default non-pressurised state. The nozzle orifice 9*a* will thus again become closed.

As can be understood from the above, a plurality of first orifices 7*a* serves the nozzle orifice 9*a*. In particular, fluid F from a plurality of first orifices 7*a* serves the nozzle orifice 9*a*. For example, all of the first orifices 7*a* may serve a single nozzle orifice 9*a*. Further, multiple nozzle orifices 9*a* may be formed in the nozzle layer 9, but the number of first orifices 7*a* is always significantly greater than the number of nozzle orifices 9*a*.

FIG. 2*a* shows another example of a spray nozzle chip configured to be installed in a medicament delivery device. The spray nozzle chip 1-1 is similar in structure to the example provided in FIG. 1*a*. The spray nozzle chip 1-1 however further comprises a sealing layer 15. The sealing layer 15 is configured to seal, for example hermetically seal, the nozzle orifice 9*a* before initial use of the spray nozzle chip 1-1. The sealing layer 15 is provided, e.g. coated or deposited, on an outer surface of the nozzle layer 9. The outer surface of the nozzle layer 9 faces away from the first layer 7. The sealing layer 15 may follow the structure of the nozzle layer 9 and thus the sealing layer 15 may not entirely fill up the nozzle orifice 9*a*. The sealing layer 15 attaches to the continuous surface 7*b* of the first layer 7, which continuous surface 7*b* is aligned with the nozzle orifice 9*a* in a direction along the central axis A. According to one example, the sealing layer 15 may have an essentially uniform thickness along its extension on the nozzle layer 9.

The sealing layer 15 may be antibacterial. Hereto, the sealing layer 15 may for example comprise silver, or consist of silver. Alternatively, or additionally, the sealing layer 15 may comprise a hydrophobic component for repelling a fluid F.

When initially used, the pressure provided by the fluid F causes the nozzle layer 9 to flex away from the first layer 7 and the sealing layer 15 to rupture, as shown in FIG. 2*b*. The fluid F will thus be atomised in the same manner as has been described with reference to FIG. 1*b* once the sealing layer 15 has ruptured. The rupturing of the sealing layer 15 may result in that a sealing layer portion 15*a* of the ruptured sealing layer 15 remains attached to the continuous surface 7*b* of the first layer 7. The sealing layer portion 15*a* forms a protruding structure on the first layer 7. The nozzle layer 9 may hence be in direct contact with and rest against the sealing layer portion 15*a* when the nozzle layer 9 returns to its default non-pressurised state. Hereto, the sealing layer portion 15*a* may act as a valve seat and may close the nozzle orifice 9*a* in the default non-pressurised state.

FIG. 3 shows another example of a spray nozzle chip configured to be installed in a medicament delivery device. The spray nozzle chip 1-2 is similar to the example shown in FIGS. 1*a* and 1*b*. The spray nozzle chip 1-2 however has a different configuration of the nozzle layer 9. The exemplified nozzle layer 9 is curved towards the first layer 7. This curved, bent, or concave structure towards the first layer 7 may be a bimorph-structure or induced by residual stress in the layer during manufacturing. The nozzle layer 9 and the first layer 7 may for example during manufacturing be provided with different residual stress, e.g. by using different material for the two layers 7 and 9. By proper selection of the materials, this results in that the nozzle layer 9 is biased or pre-tensioned and bends towards the first layer 7, Additionally, or alternatively, another layer may be added onto the nozzle layer, which shows compressive stress and forces the nozzle layer towards the first layer. It is to be noted that the nozzle layer does not have to be curved or bent to obtain a valve functionality using built-in stress. Thus, the nozzle orifice perimeter 9*b* will by default be pressed towards the continuous surface 7*b* of the first layer 7 when the nozzle layer 9 is in the default non-pressurised state. When the spray nozzle chip 1-2 is in use, i.e. during a spraying operation, the nozzle layer 9 will flex away from the first layer 7 in a similar manner as in the previous two examples. Fluid may thus be dispensed via the spray nozzle chip 1-2. The pre-tensioned nozzle layer 9 provides a greater sealing force of the orifice perimeter 9*b* against the continuous surface 7*b*, which results in an improved seal of the nozzle orifice 9*a* when the nozzle layer 9 is in the non-pressurised state.

In addition to the configuration shown in FIG. 3, the spray nozzle chip 1-2 could according to one variation also comprise a sealing layer, like in the example discussed with reference to FIGS. 2*a* and 2*b*.

FIG. 4*a* shows another example of a spray nozzle chip. The spray nozzle chip 1-3 is similar to the previously described spray nozzle chip 1-2. The substrate 3-1 of the spray nozzle chip 1-3 however differs from the previously described substrate 3. The substrate 3-1 has a plurality of fluid supply orifices, namely a first fluid supply orifice 3-1*a* and a second fluid supply orifice 3-1*b* both of which extends to respective set of first layer orifices 7*a*. The substrate 3-1 has a separating wall 3-1*c* which separates the first fluid supply orifice 3-1*a* and the second fluid supply orifice 3-1*b*. The separating wall 3-1*c* is aligned with the nozzle orifice 9*a*, and supports the continuous surface 7*b* of the first layer 7. The continuous surface 7*b* is aligned with the nozzle orifice 9*a*. Thus, during the default non-pressurised state of the nozzle layer 9, the nozzle layer 9 rests against the continuous surface 7*b* and/or against a sealing layer portion of the ruptured sealing layer 15 if it remains attached to the continuous surface 7*b* after the sealing layer 15 has been ruptured. FIG. 4*b* shows the spray nozzle chip 1-3 in use, when the nozzle layer 9 flexes away from the first layer 7.

FIG. 5*a* shows a spray nozzle chip 1-4 which is similar to the one disclosed in FIGS. 4*a* and 4*b*. The first layer 9 in this example however comprises fewer first layer orifices 7*a*. In the example shown in FIGS. 4*a* and 4*b*, the number of first layer orifices 7*a* corresponds to the number of fluid supply orifices of the substrate 1-3. FIG. 5*b* shows the spray nozzle chip 1-4 in use.

FIGS. 6*a* to 6*c* show various examples of spray nozzle chips 1-5, 1-6, 1-7, which may or may not comprise any support layer. In case the support layer is present, the support layer can be made very thin, down to the order of Angstrom. In both cases, to ensure that the nozzle layer 9, 9-1 and the first layer 7-1, 7-2, 7-3 do not stick to each other, to allow flexing of the nozzle layer 9, 9-1 relative to the first layer 7-1, 7-2, 7-3 and thus the valve functionality, one or both of these layers have facing surfaces that have been geometrically modified. In the example in FIG. 6a, the first layer 7-1 has a surface which faces the nozzle layer 9 which has been geometrically modified. The same applies to the example in FIG. 6b. In FIG. 6a, the perimeters of the first layer orifices 7a have been rounded or bevelled in the axial direction. This reduces the surface area in contact with the opposing layer. In the example in FIG. 6b, the surface of the first layer 7-2, which faces the nozzle layer 9 has been made ribbed or irregular. In the example in FIG. 6c, the surface of the nozzle layer 9-1 facing the first layer 7 has been ribbed or made irregular. During manufacturing, the bonding between the nozzle layer and the first layer may in these cases be made by using for example fusion-bonding in selected area, i.e. laterally, so that the valve functionality is obtained. These examples may also comprise the sealing layer.

An example of manufacturing a spray nozzle chip 1, 1-1, 1-2 will now be described with reference to FIGS. 7a-d. It should be noted that the spray nozzle chip 1, 1-1, 1-2 may be manufactured according to a plurality of different processes.

In a first step a first deposition onto the substrate 3 is performed to obtain the first layer 7. Any material used in thin film depositions may be used as substrate, for example metals, silicon nitride, silicon, silicon dioxide. The first layer orifices 7a may be obtained using for example photolithography by providing a suitable patterned photoresist and etching the pattern of first layer orifices 7a into the first layer 7 using for instance reactive ion etching. The photoresist may be removed after the patterning of the first layer 7 has been completed.

A second deposition, onto the first layer 7 to obtain the support layer 11 may then be performed.

A third deposition, onto the support layer 11, is performed to obtain the nozzle layer 9. The bonding between the nozzle layer 9 and the first layer 7, via the support layer 11, may for example be via adhesive bonding or eutectic bonding. Next, the nozzle layer 9 is patterned to obtain the nozzle orifice 9a. The nozzle layer 9 may for example be patterned using photolithography by providing a suitable patterned photoresist and etching the pattern of the nozzle orifice 9a into the nozzle layer 9 using for instance reactive ion etching. The photoresist may be removed after the patterning of the nozzle layer 9 has been completed. The result of the above steps is depicted in FIG. 7a.

Next, as shown in FIG. 7b, the support layer 11 is undercut to free the continuous surface 7b of the first layer 7, which is aligned with the nozzle orifice 9a. The undercutting may for example be made using wet or dry etching. Undercutting allows for the sealing layer deposited in the next step described herein to extend below the nozzle layer 9. An alternative to undercutting is to only remove the portion of the support layer 11 which is aligned with the nozzle orifice 9 to expose the continuous surface 7a below the nozzle orifice 9, and thus performing no undercutting.

FIG. 7c shows a sealing layer deposition step. In this step, a fourth deposition onto the nozzle layer 9 is performed to obtain the hermetic sealing layer 15. The fourth deposition is performed such that the hermetic sealing layer 15 partially fills up the nozzle orifice 9a and bonds with the underlying continuous surface 7b which forms part of the first layer 7.

Turning now to FIG. 7d, the substrate 3 is etched to obtain the fluid supply orifice 3a which extends from one side of the substrate 3 to an opposite side of the substrate 3. In particular, the fluid supply orifice 3a extends the entire distance to the first layer 7 and connects with the first orifices 7a.

The support layer 11 is finally further undercut to free all of the first layer orifices 7a.

In a manufacturing variation concerning the depositions, as shown in FIG. 8, the nozzle layer 9 and the first layer 7 may be bonded using two wafers or substrates, with an auxiliary substrate 17 being provided with the nozzle layer 9 and the substrate 3 being provided with the first layer 7 by means of transfer. The auxiliary substrate 17 and the substrate 3 may be Silicon on Insulator (SOI) wafers. The nozzle layer 9 and the first layer 7 may then be bonded whereby the transfer is performed, i.e. the nozzle layer 9 is separated from the auxiliary substrate 17. This eliminates the problem of having to etch an intermediate layer/support layer through the nozzle orifice(s).

In any example herein, there may optionally be provided a silicon oxide layer between the first layer and the substrate.

Figure 9:
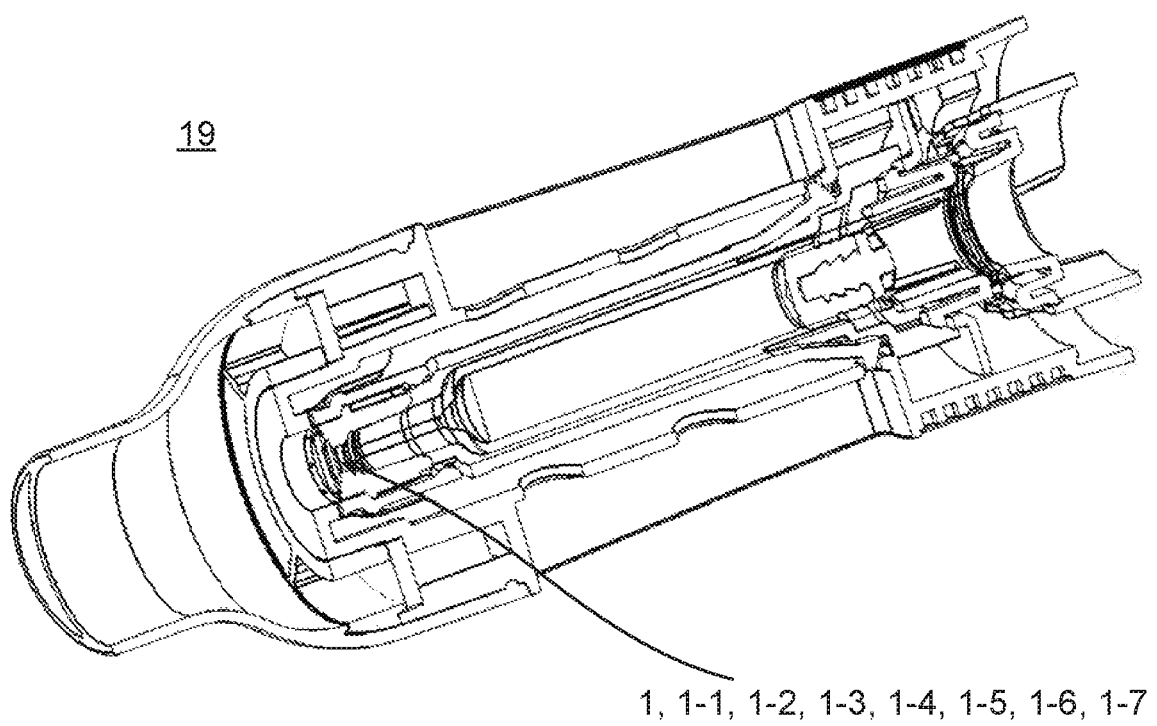
FIG. 9 depicts an example of a container holder and a medicament delivery member of a medicament delivery device comprising a spray nozzle chip.

The spray nozzle chip 1, 1-1, 1-2 may be used in medical applications. For instance, the spray nozzle chip 1, 1-1, 1-2 may be provided in a medicament delivery device such as an inhaler or an eye dispenser. FIG. 9 shows an example of a container holder and a medicament delivery member 19 of a medicament delivery device in a longitudinal section comprising the spray nozzle chip 1, 1-1, 1-2 attached to a nozzle device holder.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A spray nozzle chip comprising:
   a first layer provided with a first layer orifice; and
   a mechanically flexible nozzle layer positioned to directly face the first layer and is provided with a nozzle orifice, wherein the nozzle layer bears against the first layer when in a default non-pressurized state,
   wherein the spray nozzle chip having a valve functionality obtained by a flexing movement of the nozzle layer relative to the first layer due to pressure changes, wherein the nozzle orifice is closed when the nozzle layer is in the default non-pressurized state and wherein the nozzle orifice is opened and set in fluid communication with the first layer orifice when the nozzle layer is deformed due to pressure during a spraying operation, and
   wherein the spray nozzle chip further comprises a sealing layer that seals the nozzle orifice before initial use of the spray nozzle chip, where the sealing layer is ruptured when the nozzle layer is deformed due to applied pressure during the spraying operation.

2. The spray nozzle chip as claimed in claim 1, wherein the nozzle orifice has a nozzle orifice perimeter and wherein the nozzle orifice and the nozzle orifice perimeter are covered in the default non-pressurized state due to cooperation between the nozzle layer and the first layer.

3. The spray nozzle chip as claimed in claim 2, wherein the nozzle orifice perimeter is in contact with the first layer in the default non-pressurized state to thereby close the nozzle orifice.

4. The spray nozzle chip as claimed in claim 1, wherein the sealing layer is antibacterial.

5. The spray nozzle chip as claimed in claim 1, wherein the sealing layer comprises silver and/or a hydrophobic component.

6. The spray nozzle chip as claimed in claim 1, wherein the nozzle layer is mechanically more flexible than the first layer.

7. The spray nozzle chip as claimed in claim 1, wherein each of the first layer and the nozzle layer is a membrane layer.

8. The spray nozzle chip as claimed in claim 1, wherein the first layer is generally parallel with the nozzle layer.

9. The spray nozzle chip as claimed in claim 1, wherein the nozzle orifice has a nozzle orifice perimeter, and the nozzle layer has an internal built-in stress that presses the nozzle layer to the first layer in the default non-pressurized state to thereby cover the nozzle orifice and the nozzle orifice perimeter.

10. The spray nozzle chip as claimed in claim 1, wherein one of the first layer and the nozzle layer has a protruding structure which encircles the perimeter of the nozzle orifice and provides a sealing pressure to close the nozzle orifices in the default non-pressurized state.

11. The spray nozzle chip as claimed in claim 1, wherein one of the first layer a protruding structure; wherein the nozzle layer is in direct contact with and rest against the protruding structure when the nozzle layer returns to the default non-pressurized state.

12. The spray nozzle chip as claimed in claim 1, comprising a substrate supporting the first layer, which substrate is provided with a fluid supply orifice configured to supply fluid to the first layer orifice.

13. The spray nozzle chip as claimed in claim 1, wherein the cross-sectional area of the first layer orifice is smaller than the cross-sectional area of the nozzle orifice.

14. The spray nozzle chip as claimed in claim 1, wherein the first layer is a sieve layer comprising a plurality of first layer orifices configured to be in fluid communication with the nozzle orifice when the nozzle layer is deformed due to pressure during a spraying operation.

15. The spray nozzle chip as claimed in claim 1, wherein the spray nozzle chip comprise a support layer provided between a portion of the first layer and the nozzle layer to distance the nozzle layer from the first layer.

16. The spray nozzle chip as claimed in claim 15, wherein the support layer is a thin film layer.

17. The spray nozzle chip as claimed in claim 1, wherein the first layer has a first surface which faces a second surface on the nozzle layer; wherein the first and/or the second surface is rounded or beveled in the axial direction; or ribbed or irregular.

18. The spray nozzle chip as claimed in claim 1, wherein the nozzle chip is configured to break a passing fluid jet up into micro droplets and
wherein upon completion of the spraying operation the nozzle layer returns to the default non-pressurized state such that a portion of the sealing layer cooperates with the nozzle layer to close the nozzle orifice.

19. A medicament delivery device comprising a spray nozzle chip as claimed in claim 1.

20. The medicament delivery device as claim 19, wherein the medicament delivery device comprises a container holder and a medicament delivery member; wherein medicament delivery member comprises a nozzle device holder configured to hold the spray nozzle chip.

* * * * *